US011865358B2

United States Patent
Beerwerth et al.

(10) Patent No.: US 11,865,358 B2
(45) Date of Patent: Jan. 9, 2024

(54) SKIN TREATMENT DEVICE

(71) Applicant: Braun GmbH, Kronberg (DE)

(72) Inventors: Frank Beerwerth, Kaltenholzhausen (DE); Uwe Bielfeldt, Bad Soden (DE); Dalibor Dadic, Königstein (DE); Felix Heinemann, Frankfurt am Main (DE); Alois Koeppl, Weilrod (DE); Anette Friedrich, Mühltal (DE)

(73) Assignee: Braun GMBH, Kronberg (DE)

( * ) Notice: Subject to any disclaimer, the term of this patent is extended or adjusted under 35 U.S.C. 154(b) by 58 days.

(21) Appl. No.: 17/361,598

(22) Filed: Jun. 29, 2021

(65) Prior Publication Data
US 2022/0001199 A1    Jan. 6, 2022

(30) Foreign Application Priority Data
Jul. 1, 2020    (EP) .................................... 20183548

(51) Int. Cl.
*A61N 5/06* (2006.01)
*A45D 26/00* (2006.01)

(52) U.S. Cl.
CPC ....... *A61N 5/0617* (2013.01); *A45D 26/0004* (2013.01); *A45D 26/0028* (2013.01); *A45D 2026/008* (2013.01); *A45D 2200/1054* (2013.01)

(58) Field of Classification Search
CPC ............ A61N 5/0616; A61N 5/0617; A45D 26/0004; A45D 26/0028; A45D 2026/008; A61H 23/0245
See application file for complete search history.

(56) References Cited

U.S. PATENT DOCUMENTS

| | | | | |
|---|---|---|---|---|
| 3,756,105 A | * | 9/1973 | Balamuth | B26B 19/00 30/34.2 |
| 9,782,324 B2 | | 10/2017 | Crunick et al. | |
| 2002/0177792 A1 | | 11/2002 | Ooba et al. | |
| 2007/0173746 A1 | * | 7/2007 | Barzilay | A61N 7/00 601/2 |
| 2011/0040235 A1 | * | 2/2011 | Castel | A61F 7/00 604/20 |
| 2016/0151238 A1 | | 6/2016 | Crunick et al. | |
| 2017/0209708 A1 | | 7/2017 | Schwarz | |
| 2019/0262225 A1 | * | 8/2019 | Gertner | A61H 23/006 |

FOREIGN PATENT DOCUMENTS

| | | |
|---|---|---|
| EP | 2636399 A1 | 9/2013 |
| WO | 2011019788 A1 | 2/2011 |

OTHER PUBLICATIONS

Extended European Search Report and Search Opinion; Application No. 20183548.5; dated Dec. 17, 2020; 06 pages.
PCT Search Report and Written Opinion for PCT/IB2021/055821 dated Sep. 24, 2021, 9 pages.

* cited by examiner

*Primary Examiner* — Todd J Scherbel
(74) *Attorney, Agent, or Firm* — Stefan M. Schneider

(57) ABSTRACT

The present application is concerned with a skin treatment device that has a handle section arranged to be held in a human user's hand, a treatment head section having a skin treatment unit and a skin contact frame having a skin contact surface, the skin contact frame at least partially encircling a skin treatment area and a vibration generation unit being coupled with the skin contact frame to vibrate at least a portion of the skin contact frame at an ultrasonic frequency.

18 Claims, 1 Drawing Sheet

SKIN TREATMENT DEVICE

FIELD OF THE INVENTION

The present disclosure is concerned with skin treatment devices that have a treatment head section comprising a skin treatment unit and a skin contact frame intended for contacting the skin in operation and it is in particular concerned with such skin treatment devices that are intended for being moved while the skin contact frame is in skin contact.

BACKGROUND OF THE INVENTION

Skin treatment devices such as light-based skin treatment devices are known, where a skin contact frame must be in close contact with the skin when the skin treatment—e.g. the application of treatment light—is effected in order to avoid that intense light leaks out as such intense light might be harmful for a user's eyes. Such devices may comprise skin contact sensors that positively confirm when the skin contact frame is in close contact with the skin. In order to apply treatment light to other spots of the skin, the skin treatment device may be detached from the skin and be put into close contact with the skin at another spot. A user may consider it more convenient to move the skin treatment device over the skin, i.e. maintaining the close skin contact between skin contact frame and skin while moving the device. In order to support the motion of the skin contact frame over the skin, a material having a low frictional coefficient with the skin may be chosen or a lubricant may be applied to the skin to reduce the friction between skin and skin contact frame.

It is an object to improve the known skin treatment devices and to in particular improve the ease of use of such skin treatment devices.

SUMMARY OF THE INVENTION

In accordance with one aspect there is provided a skin treatment device that has a handle section arranged to be held in a human user's hand, a treatment head section having a skin treatment unit and a skin contact frame having a skin contact surface, the skin contact frame at least partially encircling a skin treatment area and a vibration generation unit coupled with the skin contact frame to vibrate at least a portion of the skin contact frame at an ultrasonic frequency.

BRIEF DESCRIPTION OF THE DRAWINGS

The present disclosure will be further elucidated by a detailed description of example embodiments and with reference to figures. In the FIGS.

DETAILED DESCRIPTION OF THE INVENTION

Figure 1:
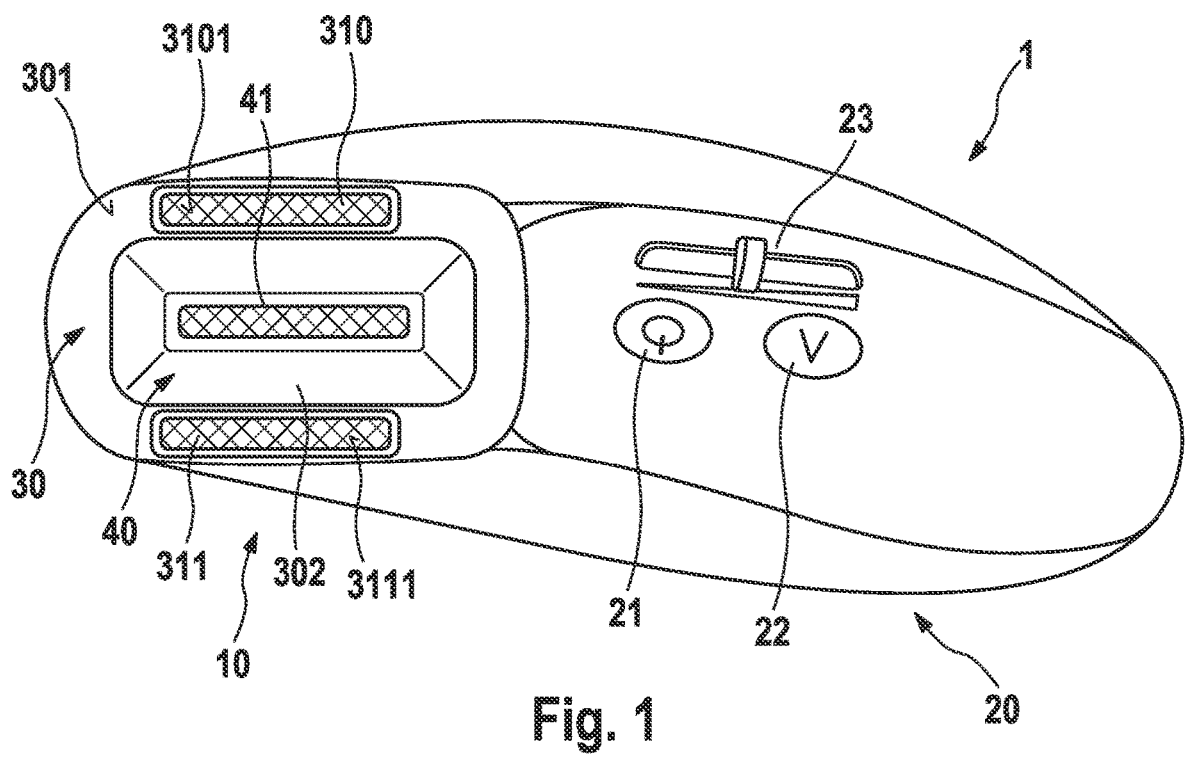
FIG. 1 is a schematic depiction of an example skin treatment device.

In accordance with the present disclosure, a skin treatment device is proposed that has a handle section and a treatment head section, where the treatment head section comprises a skin treatment unit and a skin contact frame. In some embodiments, the treatment head section is repeatedly attachable and detachable from the handle section. Additionally or alternatively, the skin contact frame is in some embodiments repeatedly attachable and detachable from the treatment head section. The skin contact frame has a skin contact surface for getting into close contact with the skin to be treated. The skin contact frame may completely encircle a skin treatment area or the skin contact frame may comprise one or several skin contact frame elements that only partly encircle a skin treatment area, e.g. the skin contact frame may comprise to oppositely positioned bar elements. The skin contact frame may also cover the skin treatment area, e.g. the skin contact frame may comprise or consist of a skin contact frame element that is transparent for treatment light that is applied onto the skin by the skin treatment device. That means that in some embodiments, the skin contact frame extends across the skin treatment area and may comprise a window for treatment light. While the skin treatment unit may comprise one or several skin treatment elements that may get into contact with the skin to perform a skin treatment such as one or several razor blades, the skin contact surface of the skin contact frame may otherwise be the only portion of the skin treatment device that is intended to contact the to be treated skin during regular operation of the skin treatment device. This shall not exclude that the handle section of course may typically be in contact with the skin of at least one of the hands of the user during operation.

The skin treatment device may be realized as one of a light-based hair removal device, a light-based skin treatment device, a manual razor, an electric shaver, an epilation device, a skin cleansing device, a skin massaging device, or a skin exfoliation device, which is to be understood as a non-limiting list of possible skin treatment devices. The skin treatment unit may comprise at least one of a light source for applying treatment light, one or several razor blades, an epilation roller, a shaver head, a trimmer, a massaging head, an exfoliation head, or a brush.

The skin contact frame may be a floatingly mounted part of the skin treatment device allowing a vibration of the skin contact frame relative to the rest of the skin treatment device, e.g. the skin contact frame may be mounted by means of at least one resilient element at a mounting portion of the skin treatment device. The at least one resilient element may be a spring such as a coil spring, a leaf spring or an elastic element such as an artificial or natural rubber element. In some embodiments, the skin contact frame comprises at least one portion that is driven into a vibration rather than driving the whole skin contact frame into vibration. The skin contact frame may comprise two or more portions that are driven into vibration such as three or four or five etc. portions. The different portions may be driven into different types of vibrations, e.g. the different portions may vibrate with a different frequency and/or amplitude or the vibrations may have different directions. The different portions may be coupled with different vibration generation elements of the vibration generation unit. In some embodiments as described above, where the skin contact frame is removable, the vibration generation unit is removable together with the skin contact frame.

It is generally known that two objects gliding with their opposed surfaces over each other may experience the so-called stick-slip phenomenon (also known as slip-stick phenomenon or simply as stick-slip), where a spontaneous jerking motion occurs instead of a continuous gliding. It is believed that this phenomenon of alternating between a sticking of the surfaces to each other and sliding over each other can be explained by separating the friction between the two surfaces into a static friction and a kinetic friction. While the static friction coefficient may typically be larger than the kinetic friction coefficient, an applied force may overcome the static friction and the reduction of the overall friction to the kinetic friction can cause a sudden increase in the velocity of the movement between the two objects. Playing of a glass harp by rubbing a wet finger along the rim of a thin walled wine glass or the like is one example of the stick-slip phenomenon.

In accordance with the present disclosure, it is proposed that at least a portion of the skin contact frame is coupled with a vibration generation unit to cause a high-frequency vibration, in particular a micro-vibration having an amplitude of between 0.1 µm to 5 µm, of at least the portion of the skin contact frame or of the complete skin contact frame. The vibration of the portion of the skin contact frame or of the complete skin contact frame shall be such that the skin surface cannot follow this vibration of the portion of the skin contact frame or of the complete skin contact frame due to its inertia so that the friction between the two surfaces (i.e. the skin surface and the skin contact surface of at least the portion of the skin contact frame or of the complete skin contact frame) is essentially always governed by the kinetic friction coefficient. It may be sufficient to just vibrate a portion of the skin contact frame (e.g. a portion representing about 10% of the skin contacting surface of the skin contact frame, 20%, 30%, 40%, 50%, 60%, 70%, 80% or 90%) to achieve the mentioned effect for the complete skin contact frame, i.e. for the complete skin contacting surface of the skin contact frame.

The vibration may have at least a linearly reciprocating component and/or an oscillatory rotational component. The vibration shall have a vector component that is parallel to the contact surface between the skin contact frame and the skin, which component may in particular be at least about 50% of the overall vibration or at least about 60%, 70%, 80%, 80% 90%, 95% or as close to about 100% as technically possible. In case of an oscillatory rotation or of an eccentric oscillatory rotation, the rotation axis may have an angle against the skin of at least about 45 degrees or of at least about 50 degrees, 60 degrees, 70 degrees, 80 degrees, 85 degrees or of about 90 degrees. The angle against the skin is of course given by the angle against the plane or slightly curved surface that is defined by the skin contact surface of the skin contact frame.

The vibration generation unit may be realized by a piezoelectric actuator, in particular by a piezoelectric ceramic actuator, where the piezoelectric ceramic material may be rigidly connected with the at least one portion of the skin contact frame or with the complete skin contact frame, respectively, depending on what is to be vibrated. In case of several skin contact frame elements that independently form together the skin contact frame, each of the skin contact frame elements may be coupled, in particular rigidly coupled with an associated vibration generation element, e.g. a piezoelectric ceramic actuator, where the vibration generation elements together for the vibration generation unit.

While the static friction between the skin contact surface of the skin contact frame and the skin surface is effectively reduced by the vibration of the at least one portion of the skin contact frame, this shall not exclude that other means to reduce the friction between the two surfaces are as well employed such as a macroscopic structure or a microscopic texture of the skin contact surface of the skin contact frame or a lubricant that is applied to the skin and/or the skin contact surface of the skin contact frame. In the latter case, the skin treatment device may be arranged to apply a lubricant to the skin. In order to enable this, the skin contact frame may comprise at least one lubricant dispensing orifice through which the lubricant can be applied onto the skin.

The vibration generation unit may be arranged to generate a vibration having a frequency of between 20 kHz and 1 MHz (i.e. a frequency in the ultrasonic range), in particular of between 20 kHz and 100 kHz such as about 30 kHz, 40 kHz, 50 kHz, 60 kHz, 70 kHz, 80 kHz, 90 kHz or any other frequency within the given ranges. The amplitude of the vibration of the skin contact frame may be in between 0.1 µm and 5.0 µm (i.e. a vibration that can be characterized as being a micro-vibration), in particular in between 0.2 µm and 2.0 µm such as about 0.3 µm, 0.4 µm, 0.5 µm, 0.6 µm, 0.7 µm, 0.8 µm, 0.9 µm, 1.0 µm, 1.1 µm, 1.2 µm, 1.3 µm, 1.4 µm, 1.5 µm, 1.6 µm, 1.7 µm, 1.8 µm or 1.9 µm or any other values in the given ranges. It was found that the amplitude A of the vibration required to effectively reduce the stick-slip of a skin contact frame with skin is inversely proportional to the frequency f, i.e. A 1/f. For example, an amplitude of 0.1 µm may be applied for a high frequency such as 1 MHz and an amplitude of 5.0 µm may be applied for a low frequency such as 20 kHz. For a frequency of 30 kHz, an amplitude of 1.0 µm may be applied.

The skin treatment device may comprise a control unit for controlling at least one or various aspects of the skin treatment device as will be discussed further below.

In some embodiments, the skin treatment device comprises at least one user-operable input or interface element such as a button, switch, touch panel or touch-sensitive display to control at least the switching ON or OFF of the vibration generation unit and/or of at least one of the amplitude or frequency of the vibration caused by the vibration generation unit. While there may be a general interest of the user to switch ON or OFF the vibration generation unit, switching OFF of the vibration of the skin contact frame may in particular lead to a "gluing" of the skin contact frame on the skin (due to a suddenly increased static friction coefficient) and thus this gluing may support the user in keeping the skin contact frame positioned at a chosen spot for applying a skin treatment, e.g. application of treatment light for skin beautification, acne treatment or temporal or permanent hair removal. The mentioned user-operable input element may be coupled with the control unit.

In some embodiments, the control unit is arranged to control at least one of the switching ON or OFF of the vibration generation unit based on at least one skin treatment parameter and/or of at least one of the amplitude or frequency of the vibration generated by the vibration generation unit. A skin treatment parameter may be treatment time (i.e. duration of the treatment from the start instance until the current time point), force applied on the skin contact frame or motion or speed or velocity of the skin treatment device, in particular motion of the skin contact frame relative to the skin. The skin treatment device may thus comprise a clock function, a force sensor for measuring the force applied against the skin contact frame and/or a motion sensor to determine the motion of the skin treatment device, in particular motion of the skin contact frame relative to the skin. In case of a force sensor, the force sensor may be realized by a capacitive force sensor. In case of a motion sensor, the motion sensor may be realized by at least one inertial sensor (e.g. accelerometer, gyroscope and/or magnetometer) and/or by an optical sensor as is generally known from an optical computer mouse.

As the static friction between two surfaces tends to become increased by a force pushing one of the surfaces onto the other surface, the control unit may be arranged to change at least one of the amplitude or frequency in dependence on the force applied on the skin contact frame to, e.g., adapt the anti-stick-slip effect to the value of the applied force. The control unit may also be arranged to switch OFF the vibration generation unit when the force applied on the skin contact frame increases above a threshold value, assuming that the user wants to perform a skin treatment at the current spot. Once the vibration is switched OFF, the "gluing effect" as described above takes place and allows to apply the treatment at the current spot.

The control unit may be arranged to switch OFF the vibration generation unit if the skin contact frame was moved a certain distance between a previous treatment position and the current position. The control unit may also be arranged to then switch ON a skin treatment element of the skin treatment unit to provide a skin treatment on the current spot, e.g. the skin treatment element may be a light source for applying a treatment light. Generally, the control unit may be arranged to synchronize operation of the vibration generation unit and of the skin treatment element.

FIG. 1 is a schematic depiction of an example skin treatment device 1 realized as a light-based skin treatment device for emitting treatment light from a skin treatment unit 40 comprising a skin treatment element 41 realized as a flash lamp. The skin treatment device 1 comprises a treatment head section 10 and a handle section 20. The treatment head section 20 comprises a skin contact frame 30 having a skin contact surface 301 and the skin contact frame 30 here completely encircles a skin treatment area 302 that in the shown embodiment is realized as a light exit window through which light from the skin treatment element 41 can be applied onto the skin of the user.

The skin contact frame 30 as shown in FIG. 1 comprises two portions 310 and 311, where portion 310 has a skin contact surface 3101 forming a part of the complete skin contact surface 301 of the skin contact frame and the portion 311 has a respective skin contact surface 3111. In at least one mode, the complete skin contact frame 30 including the portions 310 and 311 can be driven to vibrate by a vibration generation unit and in at least one other mode only one or both of the portions 310 and 311 is driven to vibrate. In at least one mode, the skin contact frame is differently driven to vibrate than the portion 310 or the portions 310 and 311. The embodiment of FIG. 1 is understood to be not limiting.

The skin treatment device 1 here comprises a first user operable input element 21 that may be realized as an ON/OFF button for the complete device and a second user-operable input element 22 that may be realized as an ON/OFF button for the vibration generation unit. A third user-operable input element 23 may be realized as a slider for varying the frequency of the vibration caused by the vibration generation unit.

Figure 2:
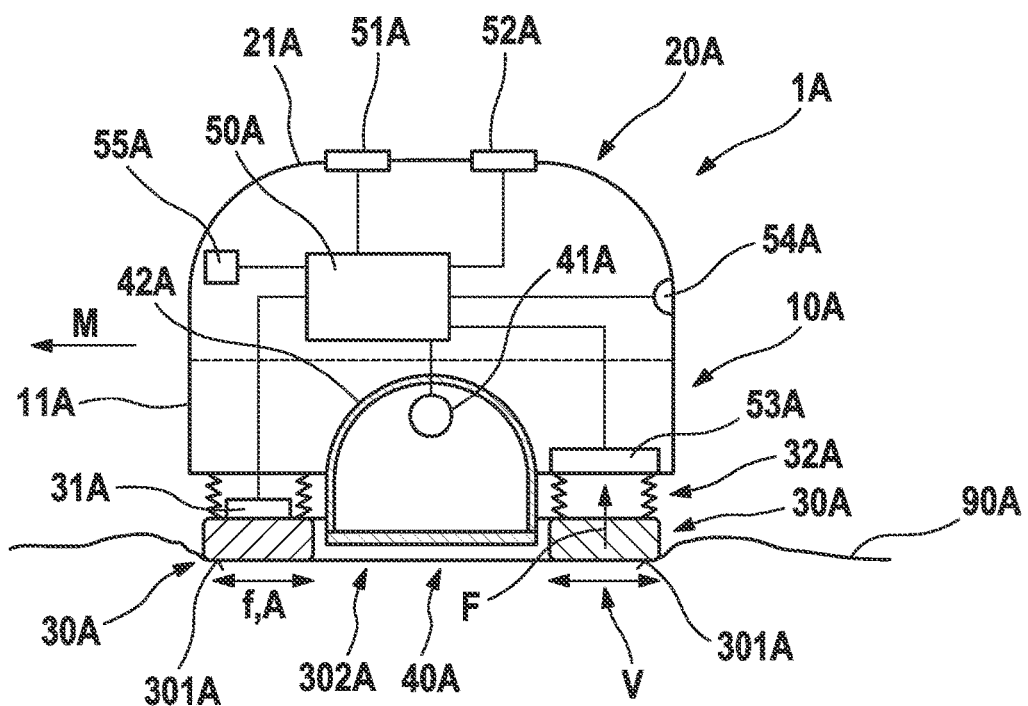
FIG. 2 is a schematic depiction of an example skin treatment device applied on the skin of a user, where components of the skin treatment device are indicated.

FIG. 2 is a schematic depiction of an example skin treatment device 1A and of several of its components. The skin treatment device 1A comprises a treatment head section 10A and a handle section 20A having a handle housing 21A that may be arranged so that it can be conveniently grasped by a user's hand. The skin treatment device 1A comprises a skin contact frame 30A that is here shown during operation of the skin treatment device 1A as being in contact with a to be treated skin surface 90A, which skin contact frame 30A is coupled with a vibration generation unit 31A. The skin treatment device 1A also comprises a skin treatment unit 40A comprising a skin treatment element 41A and a skin treatment unit housing 42A, and further a control unit 50A being coupled with various user-operable input elements 51A, 52A, sensors 53A, 55A and an indicator element 54A.

In the shown example, the skin contact frame 30A is floatingly mounted at a mounting structure 11A of the treatment head section 10A by means of resilient elements 32A. The skin contact frame 30A encircles a skin treatment area 302A through which the skin treatment can be effected—here the application of treatment light emitted by the skin treatment element 41A. The vibration generation unit 31A may be realized as a piezoelectric ceramic actuator. The operation of the vibration generation unit 31A is controlled by the control unit 50A. The vibration generation unit 31A may here cause the complete skin contact frame 30A to vibrate essentially parallel to the skin contact surface 301A of the skin contact frame 30A as is indicated by double arrows V. The vibration may be characterized by a frequency f and an amplitude A. This should not be understood as limiting as the vibration generation unit 31A may instead cause a vibration having non-deterministic changes of frequency and amplitude within certain ranges. The skin treatment device 1A here comprises a first user-operable input element 51A to switch ON and OFF the skin treatment device 1A. The skin treatment device 1A here also comprises a second user-operable input element 52A by which a user may be enabled to change the frequency f and/or the amplitude A of the vibration caused by the vibration generation unit 31A, either to optimize the effect of the reduction of the static friction and/or to customize the operation to the user's preferences. In some embodiments, a change of one of the frequency f or amplitude A may result in an inversely proportional change of the other one of the frequency f or amplitude A.

The skin treatment device 1A here comprises the force sensor 53A for measuring a force F with which the skin contact frame 30A is pushed against the skin surface 90A. The user may apply a force F above a threshold value to thereby effect that the control unit 50A switches OFF the vibration generation unit 31A so that the static friction between the skin contact surface 301A of the skin contact frame 30A and the skin surface 90A leads to s sticking or gluing of the skin contact frame 30A on the skin. As the user can then not easily move the skin treatment device 1A further over the skin, the skin treatment is performed at the spot that the user chose. Additionally and/or alternatively, the control unit 50A may be arranged to automatically stop the vibration generation unit 31A, e.g. when the motion sensor 55A has determined that the skin treatment area 49A was moved over the skin to a skin area that is adjacent to the previously treated skin area. At least one indicator element MA may be arranged on the handle section housing 21A to indicate information to the user, e.g., that a skin treatment is currently being performed.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin treatment device being a light-based hair removal device or a light-based skin treatment device, comprising:
   a handle section being arranged to be held in a human user's hand;
   a treatment head section having a skin treatment unit comprising a light source and a skin contact frame having a skin contact surface, the skin contact frame at least partially encircling a skin treatment area; and
   a vibration generation unit being coupled with the skin contact frame to cause a vibration of at least a portion of the skin contact frame at an ultrasonic frequency essentially parallel to the skin contact surface to effectively reduce a stick-slip or static friction of the skin contact frame, wherein the vibration generation unit is configured such that a change to one of an amplitude or a frequency of the vibration results in an inversely proportional change to the other of the amplitude or the frequency of the vibration;
   wherein the skin treatment device comprises a control unit that is configured to alter at least one of the amplitude or the frequency based on motion of the skin contact frame relative to a user's skin.

2. The skin treatment device in accordance with claim 1, wherein the vibration generation unit comprises a piezoelectric actuator.

3. The skin treatment device in accordance with claim 1, wherein the vibration of the skin contact frame caused by the vibration generation unit comprises at least a linear reciprocating vibration component.

4. The skin treatment device in accordance with claim 1, wherein the vibration of the skin contact frame caused by the vibration generation unit comprises at least an oscillatory rotation component around a rotation axis.

5. The skin treatment device in accordance with claim 1, wherein the frequency of the vibration is in between about 20 kHz and about 1 MHz.

6. The skin treatment device in accordance with claim 5, wherein the frequency of the vibration is in between about 20 kHz and about 100 kHz.

7. The skin treatment device in accordance with claim 1, wherein the amplitude of the vibration is in between about 0.1 μm to about 5.0 μm.

8. The skin treatment device in accordance with claim 7, wherein the amplitude of the vibration is in between about 0.2 μm and about 2.0 μm.

9. The skin treatment device in accordance with claim 1, wherein the skin treatment device comprises at least one user-operable input element for controlling at least one of the amplitude or the frequency of the vibration.

10. The skin treatment device in accordance with claim 1, wherein the skin treatment device comprises a sensor for determining a force acting on the skin contact frame.

11. The skin treatment device in accordance with claim 1, wherein the skin treatment device comprises the control unit that is arranged to control the vibration generation unit based on a skin treatment parameter.

12. The skin treatment device in accordance with claim 11, wherein the skin treatment parameter is a treatment time or a motion of the skin contact frame relative to the skin or a force acting on the skin contact frame.

13. The skin treatment device in accordance with claim 11, wherein the control unit is arranged to synchronize the control of the vibration generation unit with a control of the skin treatment unit.

14. The skin treatment device in accordance with claim 13, wherein the control unit is arranged to switch on the skin treatment unit when the vibration generation unit is switched off.

15. The skin treatment device in accordance with claim 1, wherein the skin treatment device comprises at least one user-operable input element for controlling at least one aspect of the vibration generation unit.

16. The skin treatment device in accordance with claim 15, wherein the user-operable input element is arranged for switching the vibration generation unit ON and OFF.

17. The skin treatment device in accordance with claim 1, wherein the skin treatment device comprises at least one sensor for determining a motion of the skin treatment device.

18. The skin treatment device in accordance with claim 1, wherein the control unit is further configured to switch off the vibration generation unit based on movement of the skin contact frame by a predefined distance between a current position and a previous treatment position.

* * * * *